US010390851B2

(12) United States Patent
Chu (10) Patent No.: US 10,390,851 B2
(45) Date of Patent: Aug. 27, 2019

(54) RETRIEVAL DEVICES AND RELATED METHODS OF USE

(71) Applicant: Boston Scientific Scimed, Inc., Maple Grove, MN (US)

(72) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 138 days.

(21) Appl. No.: 15/197,304

(22) Filed: Jun. 29, 2016

(65) Prior Publication Data

US 2017/0000506 A1    Jan. 5, 2017

Related U.S. Application Data

(60) Provisional application No. 62/186,718, filed on Jun. 30, 2015.

(51) Int. Cl.
*A61B 17/22* (2006.01)
*A61B 17/221* (2006.01)
*A61B 17/00* (2006.01)

(52) U.S. Cl.
CPC .... *A61B 17/221* (2013.01); *A61B 2017/0042* (2013.01); *A61B 2017/00862* (2013.01);
(Continued)

(58) Field of Classification Search
CPC .......... A61B 17/221; A61B 2017/0042; A61B 2017/22035; A61B 2017/00862; A61B 2017/2212; A61B 2017/2215
See application file for complete search history.

(56) References Cited

U.S. PATENT DOCUMENTS 5,201,741 A * 4/1993 Dulebohn ........ A61B 17/32056
606/110
5,906,622 A * 5/1999 Lippitt ................. A61B 17/221
606/113
(Continued)

FOREIGN PATENT DOCUMENTS

EP          2 949 277 A1   12/2015
WO     WO 98/48710 A1   11/1998
(Continued)

OTHER PUBLICATIONS

International Search Report and Written Opinion for corresponding International Application No. PCT/US2016/040140, dated Sep. 19, 2016 (11 pages).

*Primary Examiner* — Amy R Weisberg
(74) *Attorney, Agent, or Firm* — Bookoff McAndrews, PLLC (57) ABSTRACT

A retrieval device may have a contracted state and an expanded state. The retrieval device may include a sheath and at least three support members. Each of the support members may have a first portion with a first cross-sectional shape and a second portion with a second cross-sectional shape different from the first cross-sectional shape. A proximal end fixed of each of the support members may be coupled to the sheath, and a distal end may be movable relative to the sheath. The retrieval device may further include at least three movable members movable relative to the support members. Each movable member may extend through a lumen of one support member of the at least three support members and through a lumen of a different support member of the at least three support members.

20 Claims, 6 Drawing Sheets

(52) U.S. Cl.
CPC ............... *A61B 2017/2212* (2013.01); *A61B 2017/2215* (2013.01); *A61B 2017/22035* (2013.01)

(56) References Cited

U.S. PATENT DOCUMENTS

| | | | | |
|---|---|---|---|---|
| 5,924,175 | A * | 7/1999 | Lippitt | A61B 17/221 24/537 |
| 7,041,108 | B2 * | 5/2006 | Lippitt | A61B 17/221 604/264 |
| 7,210,210 | B2 | 5/2007 | Lippitt et al. | |
| 9,724,113 | B2 * | 8/2017 | Chu | A61B 17/221 |
| 9,808,268 | B2 * | 11/2017 | Campbell | A61B 17/221 |
| 9,808,269 | B2 * | 11/2017 | Budiman | A61B 17/221 |
| 2002/0133170 | A1 | 9/2002 | Tsuruta | |
| 2003/0225419 | A1 * | 12/2003 | Lippitt | A61B 17/221 606/127 |
| 2004/0215212 | A1 * | 10/2004 | Teague | A61B 17/221 606/127 |
| 2015/0066047 | A1 | 3/2015 | Chu et al. | |
| 2015/0066049 | A1 * | 3/2015 | Chu | A61B 17/221 606/127 |
| 2015/0148813 | A1 * | 5/2015 | Campbell | A61B 17/221 606/127 |
| 2015/0148814 | A1 * | 5/2015 | Chu | A61B 17/221 606/127 |
| 2015/0164522 | A1 * | 6/2015 | Budiman | A61B 17/221 606/113 |
| 2015/0190157 | A1 * | 7/2015 | Chu | A61B 17/22031 606/127 |
| 2015/0190190 | A1 | 7/2015 | Chu | |
| 2015/0196311 | A1 * | 7/2015 | Chu | A61B 17/221 606/127 |
| 2015/0327878 | A1 * | 11/2015 | Chu | A61B 17/22031 606/127 |
| 2016/0166270 | A1 * | 6/2016 | Hera | A61B 17/221 606/127 |
| 2016/0199079 | A1 * | 7/2016 | Chu | A61B 17/221 606/127 |
| 2016/0278797 | A1 * | 9/2016 | Rohan | A61B 17/221 |
| 2017/0000506 | A1 * | 1/2017 | Chu | A61B 17/221 |
| 2017/0281205 | A1 * | 10/2017 | Chu | A61B 17/22031 |

FOREIGN PATENT DOCUMENTS

| | | |
|---|---|---|
| WO | WO 2015/103189 A1 | 7/2015 |
| WO | WO 2015/106131 | 7/2015 |
| WO | WO 2015/175782 A1 | 11/2015 |
| WO | WO 2016/112199 A1 | 7/2016 |

* cited by examiner

RETRIEVAL DEVICES AND RELATED METHODS OF USE

CROSS-REFERENCE TO RELATED APPLICATIONS

This patent application claims the benefit of priority under 35 U.S.C. § 119 to U.S. Provisional Patent Application No. 62/186,718, filed Jun. 30, 2015, which is herein incorporated by reference in its entirety.

TECHNICAL FIELD

Various examples of the present disclosure relate generally to retrieval devices and related systems and methods. More specifically, the present disclosure relates to devices, systems, and methods for retrieving objects within a patient.

BACKGROUND

Retrieval devices are often used to remove organic material (e.g., blood clots, tissue, and biological concretions such as urinary, biliary, and pancreatic stones) and inorganic material (e.g., components of a medical device or other foreign matter), which may obstruct or otherwise be present within a patient's body cavities or passages. For example, concretions can develop in certain parts of the body, such as in the kidneys, pancreas, ureter, and gallbladder. Minimally invasive medical procedures are used to remove these concretions through natural orifices, or through an incision, such as during a percutaneous nephrolithotomy ("PNCL") procedure. Further, lithotripsy and ureteroscopy, for example, are used to treat urinary calculi (e.g., kidney stones) in the ureter of a patient.

Retrieval devices may include end effectors for manipulating objects. An exemplary end effector may have a plurality of arms that support a front loop that forms when the end effector is opened. The size of the front loop may limit the size of an object that can be captured, repositioned, and/or released from the end effector. For some procedures, there may be a need to increase the size of a front loop of an end effector to facilitate the capturing, repositioning, and/or releasing of larger objects. It may also be desirable to have an end effector close back down to a low-profile state to facilitate insertion and withdrawal of the end effector into and from a target area, and/or to capture, reposition, and/or release smaller objects. Further, during a procedure, one or more portions of the front loop may entangle with one another thereby distorting the end effector and potentially reducing its effectiveness and life span. Thus, there remains a need for retrieval devices with improved capabilities.

Further, known medical retrieval devices are complex, requiring many components and/or labor-intensive manufacturing processes. The assembly of small parts often requires visual magnification and specialized training. The available joining mechanisms can increase the profile of the medical retrieval devices beyond optimal design parameters, and may be the weakest structural points. These drawbacks can result in medical retrieval devices that are bulky, expensive, and prone to failure.

The systems and methods of the current disclosure may address some of the deficiencies described above and/or other problems in the art.

SUMMARY

In one example, a retrieval device may have a contracted state and an expanded state. The retrieval device may include a sheath and at least three support members. Each of the support members may have a first portion with a first cross-sectional shape and a second portion with a second cross-sectional shape different from the first cross-sectional shape. A proximal end fixed of each of the support members may be coupled to the sheath, and a distal end may be movable relative to the sheath. The retrieval device may further include at least three movable members movable relative to the support members. Each movable member may extend through a lumen of one support member of the at least three support members and through a lumen of a different support member of the at least three support members.

The retrieval device may additionally or alternatively include one or more of the following features: the cross-sectional shape of the first portion may be circular and the cross-sectional shape of the second portion may be ovular, the first portion may be positioned adjacent the distal end and the second portion may be positioned adjacent the proximal end; the second portion may be positioned along the support member between two separate and distinct first portions; the lumen of each support member along the second portion may be sized so as to prevent the movable members received therethrough from rotating about one another; each support member may be comprised of polyimide, PET, or combinations thereof. a transition portion between the first portion and the second portion of each of the support members; each of the at least three movable members may be configured to slide distally within one or more of the at least three support members during transition of the retrieval device from the contracted state to the expanded state; each support member may be parallel to a longitudinal axis of the sheath while the retrieval device is in the contracted state; each support member may be configured to bow radially outward from a longitudinal axis of the sheath in the expanded state; the sheath may encompass at least a portion of the movable members and at least a portion of the support members; a stop located at an end of at least one movable member to restrict movement of the end after moving a distance distally; the stop may include a coupling securing ends of the at least three movable members together; each of the at least three movable members may include a U-shaped bend located distally of the distal ends of the at least three support members; and the U-shaped bend may be preformed and urge the support members toward the contracted state.

In another example, a retrieval device may include a sheath and at least three support members. Each of the support members may taper from a first portion with a circular cross-sectional shape to a second portion with a ovular cross-sectional shape. Additionally, each of the support members may be movable between a contracted configuration extending along a longitudinal axis of the sheath in the contracted configuration, and an expanded configuration bowing radially outward from the longitudinal axis of the sheath. The retrieval device may further include at least three movable members. Each movable member may form a bridge between two different support members of the at least support members.

The retrieval device may additionally or alternatively include one or more of the following features: the first portion may be positioned adjacent a distal end of the support members and the second portion may positioned adjacent a proximal end of the support members; the retrieval device may include three bridges formed by the at least three movable members, wherein the three bridges may form a distally-facing loop when the support members are in the expanded configuration; and each bridge may form a side loop with the two support members that the bridge is between.

In another example, a method for retrieving an object using a retrieval device is disclosed. The retrieval device may include a sheath and at least three support members. Each of the at least three support members may have a varied cross-sectional shape along a length of the support members, a proximal end fixed to the sheath, a distal end movable relative to the sheath, and at least three movable members movable relative to the support members. Each movable member may extend through a lumen of one support member of the at least three support members and through a lumen of a different support member of the at least three support members. The method may include moving the movable members distally to transition the retrieval device from a contracted state to an expanded state.

It is understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate examples of the present disclosure and together with the description, serve to explain the principles of the disclosure.

DETAILED DESCRIPTION

The present disclosure is drawn to retrieval devices and related systems and methods. Reference will now be made in detail to examples of the present disclosure, examples of which are illustrated in the accompanying drawings. Wherever possible, the same reference numbers will be used throughout the drawings to refer to the same or like parts. The term "distal" refers to a location farther away from a user when introducing a device into a patient. By contrast, the term "proximal" refers to a location closer to the user when placing the device into the patient.

Examples

Figure 1:
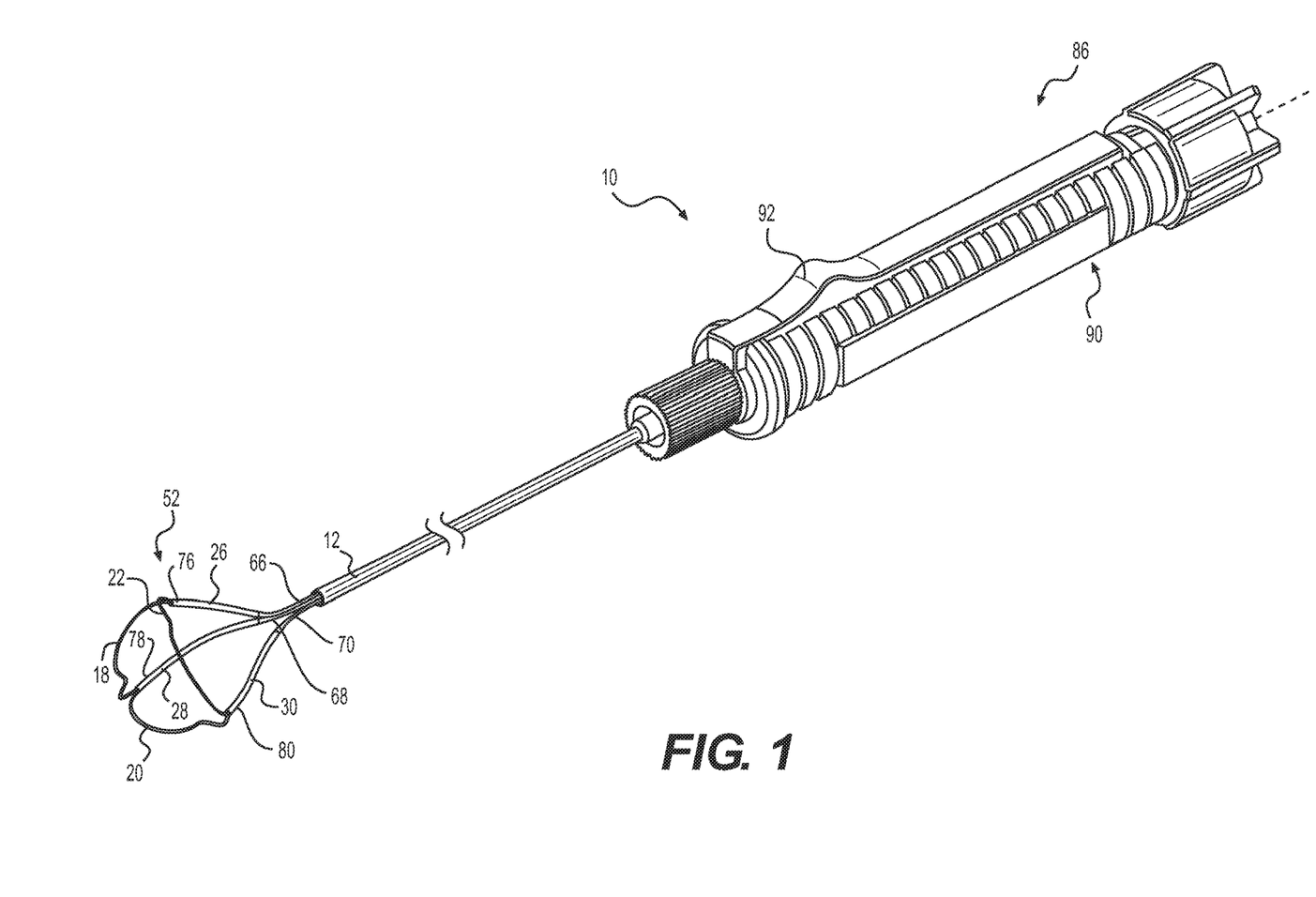
FIG. 1 is a full view of a retrieval device in an extended and expanded state.

FIG. 1 shows a full retrieval device 10, and FIGS. 2-6 show various portions of the retrieval device 10. Referring to FIG. 1, the retrieval device 10 may include a basket portion or grasper portion 52 including a plurality of movable members 18, 20, and 22, and a plurality of support members 26, 28, and 30. A proximal end 66, 68, and 70 of the support members 26, 28, and 30, respectively may be coupled to an outer sheath 12 and a handle assembly 90 while distal ends 76, 78, and 80 extend distally thereof. The handle assembly 90 may be disposed at a proximal end 86 of the retrieval device 10. The movable members 18, 20, and 22 may be coupled to the handle assembly 90 and extend through the support members 26, 28, and 30 and the outer sheath 12. As explained in more detail below, movement of an actuator 92 of the handle assembly 90 may cause relative movement between the movable members 18, 20, and 22, and the support members 26, 28, and 30 so as to transition the grasper portion 52 between an expanded state (FIGS. 1 and 2) and a contracted state (FIGS. 3-6).

Referring to FIGS. 3-6, the outer sheath 12 of retrieval device 10 may include a lumen 14 extending longitudinally therethrough. The outer sheath 12 may be, for example, a hollow tube of about 1.7-1.9 French, although the dimensions may differ based on the type of procedure being performed with the retrieval device 10. In another example, the outer sheath 12 may be a hollow tube of about 1.7 to 1.9 French. As used herein, the terms "about," "substantially," and "approximately," indicates a range of values within +/−5% of the stated value. The outer sheath 12 may be made of a polymer material or combination of materials. A proximal portion of the outer sheath 12 may be made of a different material than a distal portion of the outer sheath 12. For example, the distal portion of the outer sheath 12 may be made of a material that is more flexible than the material of the proximal portion of the outer sheath 12.

The retrieval device 10 may also include a drive member or shaft 16. The drive member 16 may extend through the lumen 14 of the outer sheath 12. The drive member 16 may be elongated, and may include, for example, a wire, braid, cable, shaft, and/or any other suitable drive member configured to receive or transfer compression, tension, and/or torsional forces. The drive member 16 may have any suitable cross-sectional shape, including cylindrical, elliptical, polygonal, and/or irregular. The drive member 16 may be made of metals, polymers, or a combination of materials. It is also contemplated that the drive member 16 may have a diameter of approximately 0.0125 inches (0.03175 centimeters). The drive member 16 may have other diameters, however, depending on the type of procedure being performed with the retrieval device 10.

The movable members of retrieval device 10 may include a first movable member 18, a second movable member 20, and a third movable member 22. The first movable member 18 may include a first leg 18a, a reverse or U-shaped bend 18b, and a second leg 18c. Similarly, the second movable member 20 may include a first leg 20a, a reverse or U-shaped bend 20b, and a second leg 20c. The third movable member 22 may also include a first leg 22a, a reverse or U-shaped bend 22b, and a second leg 22c. While three movable members 18, 20, and 22 are shown, one or more additional movable members may also be included. The bends 18b, 20b, and 22b may be disposed between respective first and second legs 18a and 18c, 20a and 20c, and 22a and 22c, respectively.

Each of the movable members 18, 20, and 22 may be formed of any suitable material including, but not limited to, metals, polymers, or a combination of materials. For example, one or more of the movable members 18, 20, and 22 may be formed of a shape memory material, such as Nitinol, and may be treated so as to include an internal bias causing one or more of the movable members 18, 20, and 22 to move to a preselected position in the absence of an urging force. For example, the U-shaped bends 18b, 20b, 22b of the movable members 18, 20, and 22 may be preformed such as by heat setting into the U-shaped bend shape. This preformed U-shaped bend 18b, 20b, 22b may facilitate a clamping of the distal ends of the support members together in the contracted state (FIGS. 3-6). One or more of the movable members 18, 20, and 22 may be a wire, braid, cable, or shaft having any suitable diameter, such as a diameter of about 0.003 inches (0.00762 centimeters), although other suitable diameters may alternatively be utilized.

Each of the movable members 18, 20, and 22 may have any suitable cross-sectional shape, including cylindrical, elliptical, polygonal, and/or irregular. One or more of the movable members 18, 20, and 22 may include a portion flattened, machined, extruded, drawn, and/or etched into a different profile than a remaining portion. One or more of the movable members 18, 20, and 22 may be slotted to allow deflection or directional bending. The exterior surfaces of one or more of the movable members 18, 20, and 22 may be roughened, notched, slotted, etched, sand-blasted, or otherwise modified to provide a better gripping surface.

The movable members 18, 20, and 22 may be attached to the drive member 16 at a first end. For example, proximal ends of the first legs 18a, 20a, and 22a may be attached to the distal end of the drive member 16. The attachment may be provided by one or more of a splice joint, adhesives, melting, welding, crimping, and/or any other suitable attachment mechanism. It is also contemplated that a sleeve 24 may be placed over the proximal portions of the first legs 18a, 20a, and 22a, and the distal portion of the drive member 16 to secure the elements together. The sleeve 24 may be made of a polytetrafluoroethylene like TEFLON. The sleeve 24 may be heat shrinkable onto the first legs 18a, 20a, and 22a, and the drive member 16. The sleeve 24 may have a length of about 11.5 centimeters, but it should be understood that the length and other sleeve dimensions may vary based on the type of procedure being performed with the retrieval device 10. The sleeve 24 may help gather the first legs 18a, 20a, and 22a, to avoid radially outward movement of the legs when pushed distally by the drive member 16, giving the gathered portions added strength. The proximal portions of each of the first legs 18a, 20a, and 22a may contact the proximal portions of the other first legs. Longitudinal axes of the proximal portions of the first legs 18a, 20a, and 22a may be substantially parallel.

Figure 2:
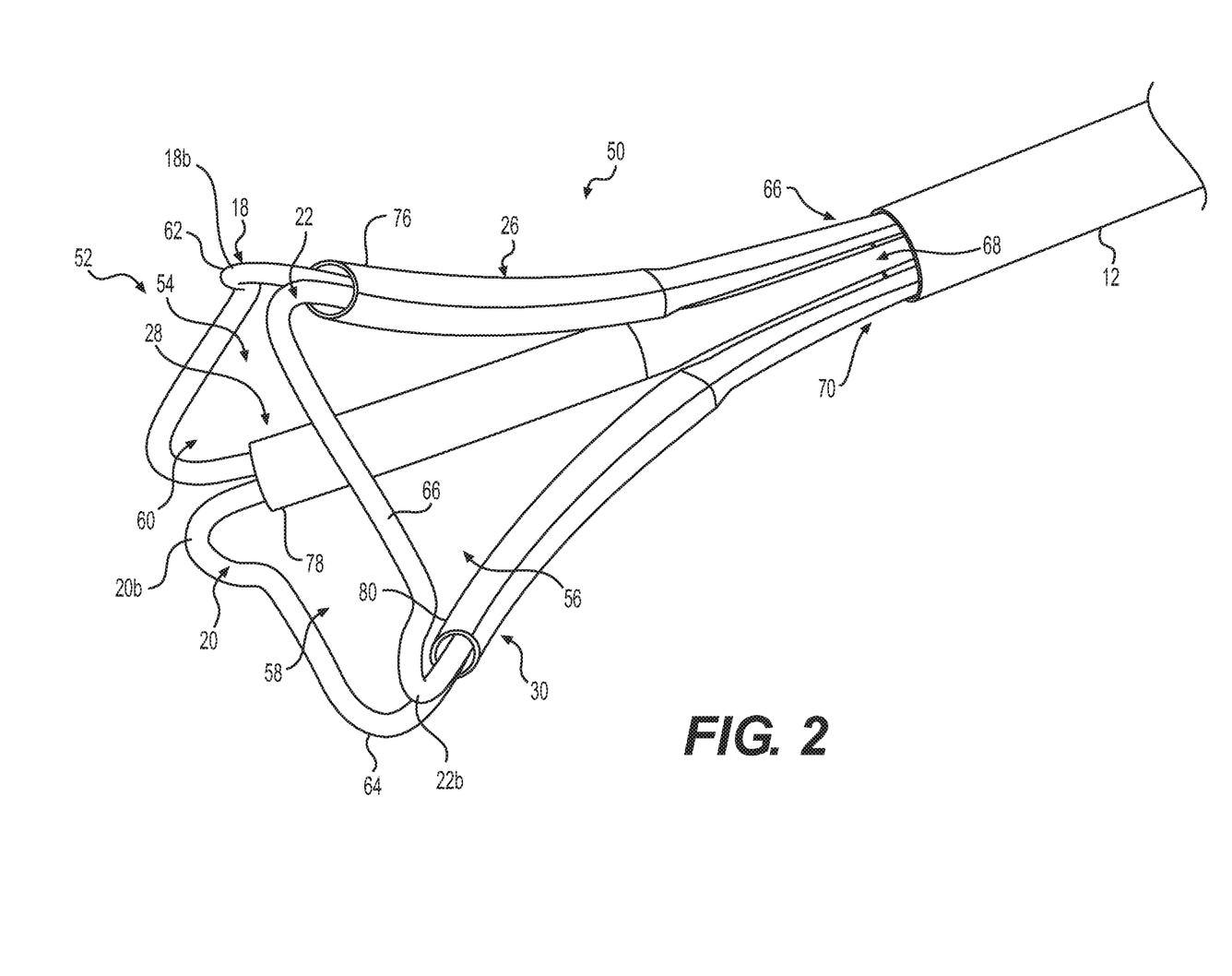
FIG. 2 is a perspective view of a distal end of the retrieval device of FIG. 1.
Figures 3, 4:
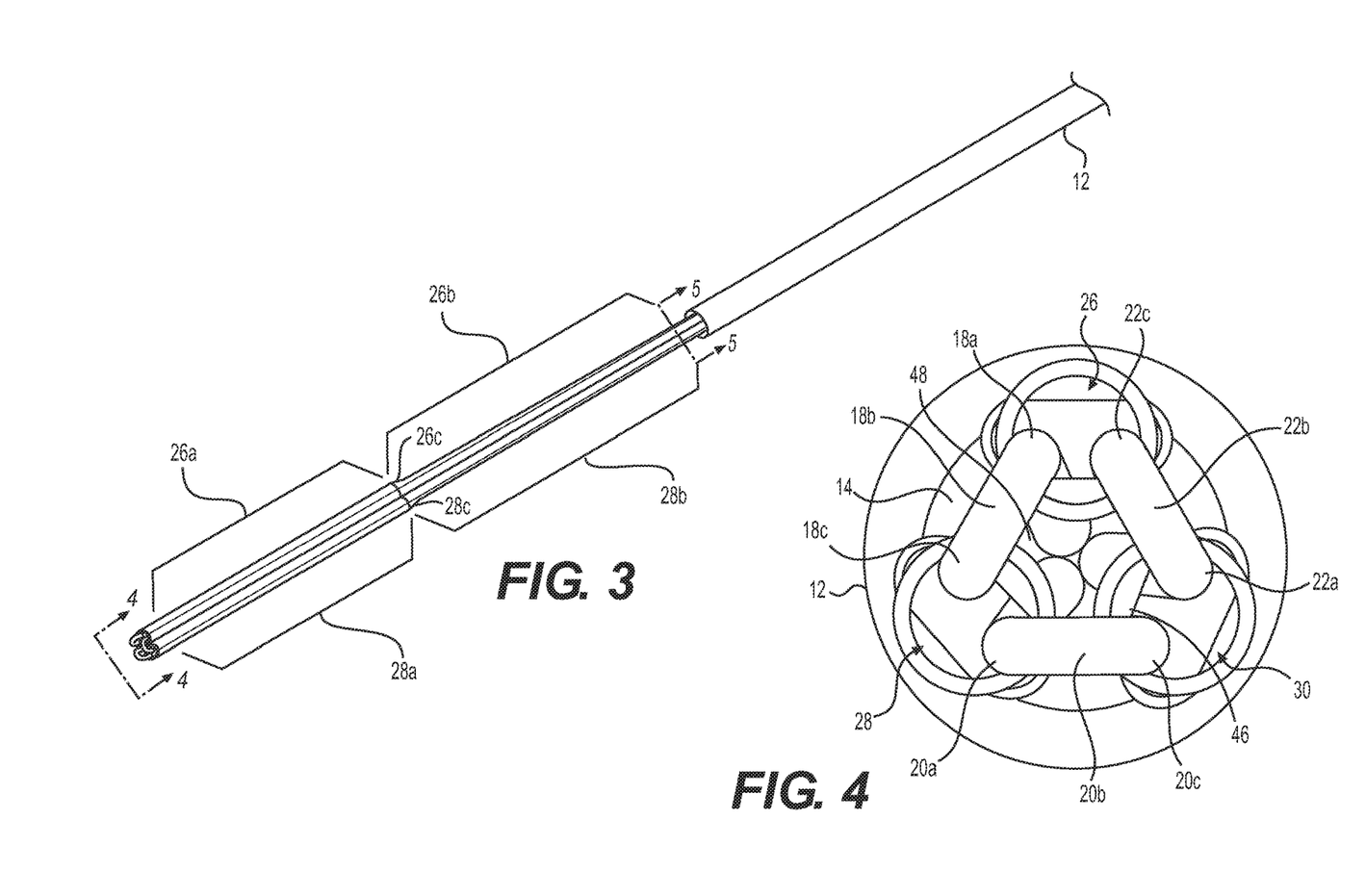
FIG. 3 is a perspective view of the distal end of the retrieval device of FIG. 1 in a retracted state, in accordance with examples of the present disclosure.
FIG. 4 is a distal end view of the retrieval device of FIG. 1, in accordance with examples of the present disclosure.
Figure 5:
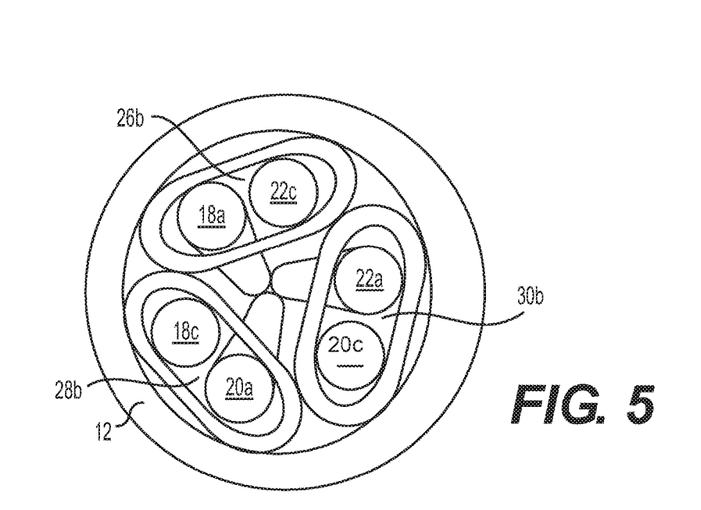
FIG. 5 is a cross-sectional view of the retrieval device of FIG. 3 along line 5-5, in accordance with examples of the present disclosure.
Figure 6:
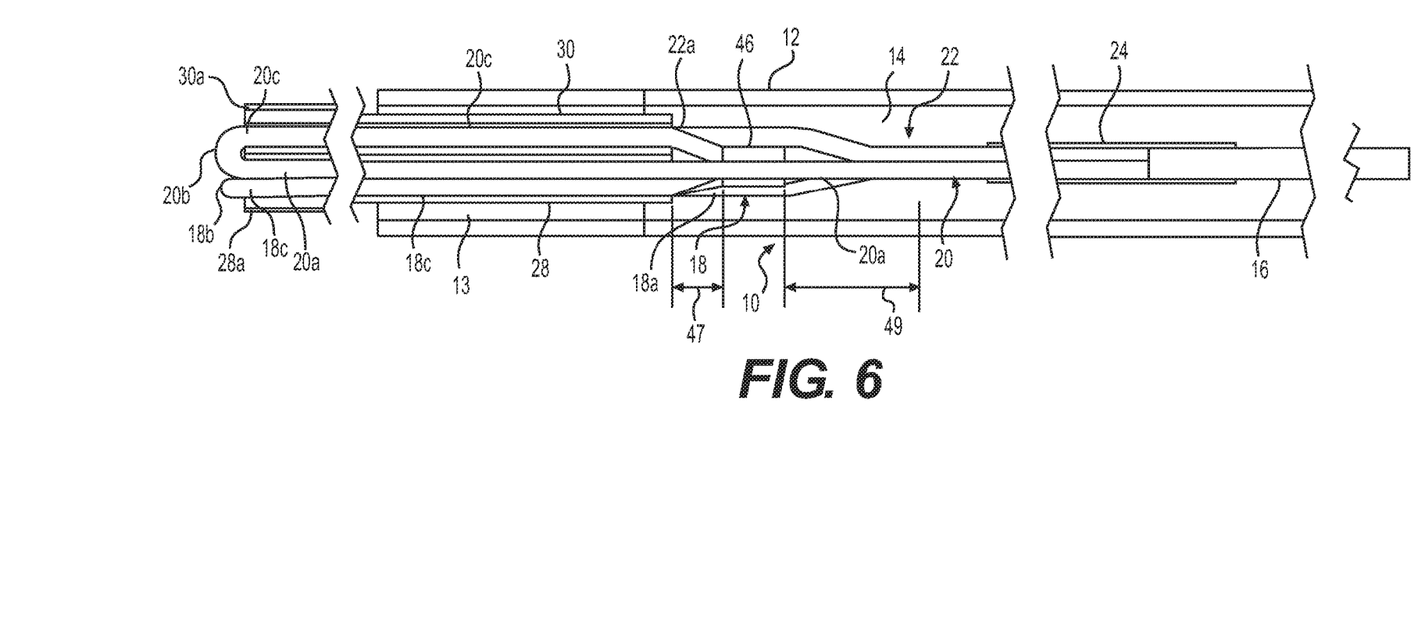
FIG. 6 is a side and partial view of the retrieval device of FIG. 1, including an end effector in a retracted and contracted state, in accordance with examples of the present disclosure.

The support members of the retrieval device 10 may include a first support member 26, a second support member 28, and a third support member 30. Each of the support members 26, 28, and 30 may have a varied cross-sectional size and/or shape. That is, for example, one or more portions of the support members 26, 28, and 30 may be flattened. For example, as shown in FIG. 3, a first portion 26a of the first support member 26 may have a circular cross-sectional shape, while a second portion 26b of the first support member 26 may have an ovular, figure-8, and/or flattened cross-sectional shape. Similarly, a first portion 28a of the second support member 28 may have a circular cross-sectional shape, while a second portion 28b of the second support member 28 may have an ovular, figure-8, and/or flattened cross-sectional shape. Further, a first portion 30a (FIG. 2) of the third support member 30 may have a circular cross-sectional shape, while a second portion 30b of the third support member 30 may have an ovular, figure-8, and/or flattened cross-sectional shape. A transition or taper portion 26c, 28c, and 30c may be positioned between respective first and second portions 26a, 26b, 28a, 28b, 30a, and 30b as shown in FIG. 3. Alternatively, the cross-sectional shape of each of the first and second portions 26a, 26b, 28a, 28b, 30a, and 30b may be circular, and each of the first portions 26a, 28a, and 30a may be larger than a respective second portion 26b, 28b, and 30b, as will be discussed in further detail below. As shown in FIGS. 2, 3, and 6, a part of each of the second portions 26b, 28b, and 30b are configured to be received within outer sheath 12, while first portions 26a, 28a, and 30a extend distally of the second portions 26b, 28b, and 30b.

Each of the support members 26, 28, and 30 may be comprised of any appropriate material, such as, for example, polyimide, PET, and combinations thereof. An inner diameter of each of the first portions 26a, 28a, and 30a, of each of the support members 26, 28, and 30, may be about 0.0065 inches (0.1651 mm) and include a wall thickness of about 0.0015 inches (0.0381 mm). Further, upon flattening, each of the second portions 26b, 28b, and 30b of each of the support members 26, 28, and 30 may be sized to tightly (e.g., snugly, closely, etc.) receive a portion of at least two moveable members 18, 20, and 22, each having a diameter of about 0.0031 inches (0.0787 mm) or less, therein and may be about 0.75 inches (19 mm) in length. As such, the at least two moveable members 18, 20, and/or 22 may have a reduced number of degrees of freedom in the second portions 26b, 28b, and 30b. For example, second portion 26b of support member 26 may be configured to receive a portion of moveable members 18 and 22, as shown in FIG. 4. Accordingly, the portion of moveable member 18 received within second portion 26b of support member 26 may be limited to axial movement along, or rotational movement about a central longitudinal axis (not shown) of moveable member 18. Additionally, the portion of moveable member 22 received within second portion 26b of support member 26 may be limited to axial movement along, or rotational movement about a central longitudinal axis of moveable member 22. That is, due to the flattening of the second portion 26b of support member 26, the portions of the moveable members 18 and 22 received within the second portion 26b may be prevented from twisting about and/or rotating about one another.

Figure 7:
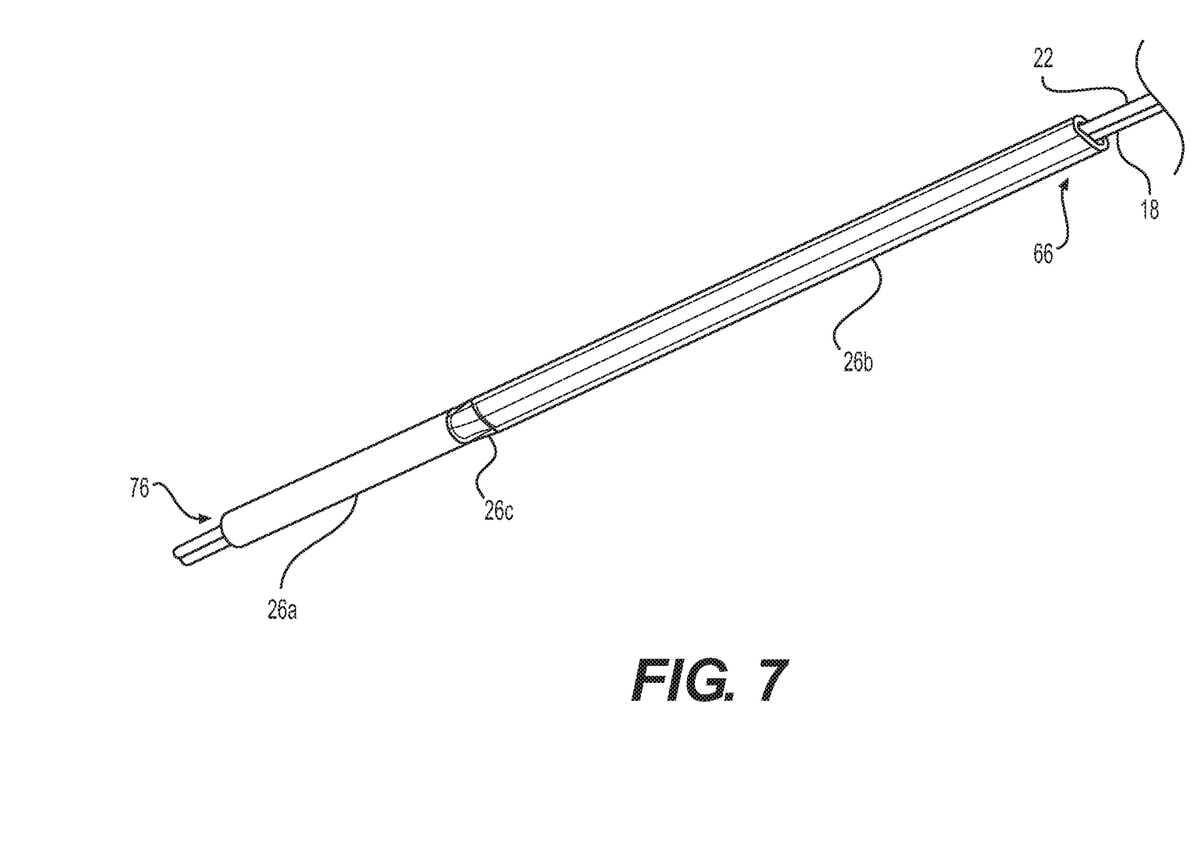
FIG. 7 is a perspective view of a support member of the retrieval device of FIG. 1.

Flattening of the second portions 26b, 28b, and 30b may be done through any appropriate means such as, for example, compressing, rolling, heat reflowing, extruding, joining and/or combinations thereof. For example, each of the second portions 26b, 28b, and 30b, of each of the support members 26, 28, and 30, may be compressed against a mandrel individually and/or simultaneously so as to alter the cross sectional shape of the second portions 26b, 28b, and 30b to an ovular cross-section shape as shown in FIGS. 2, 3 and 7. It is noted, that while each of the second portions 26b, 28b, and 30b have been described herein as ovular, the disclosure is not so limited. Rather, the second portions 26b, 28b, and 30b may be altered to have any appropriate cross-sectional shape configured to prevent the moveable members 18, 20, and 22 from twisting about and/or rotating about one another. For example, in some embodiments, the second portions 26b, 28b, and 30b may include the same cross-sectional shape as the first portions 26a, 28a, and 30a, but having a smaller diameter. That is, each of the first portions 26a, 28a, and 30a and the second portions 26b, 28b, and 30b may have a circular cross-sectional shape. However, a diameter of the each of the first portions 26a, 28a, and 30a may be larger than a diameter of the a respective second portion 26b, 28b, and 30b.

Figure 8:
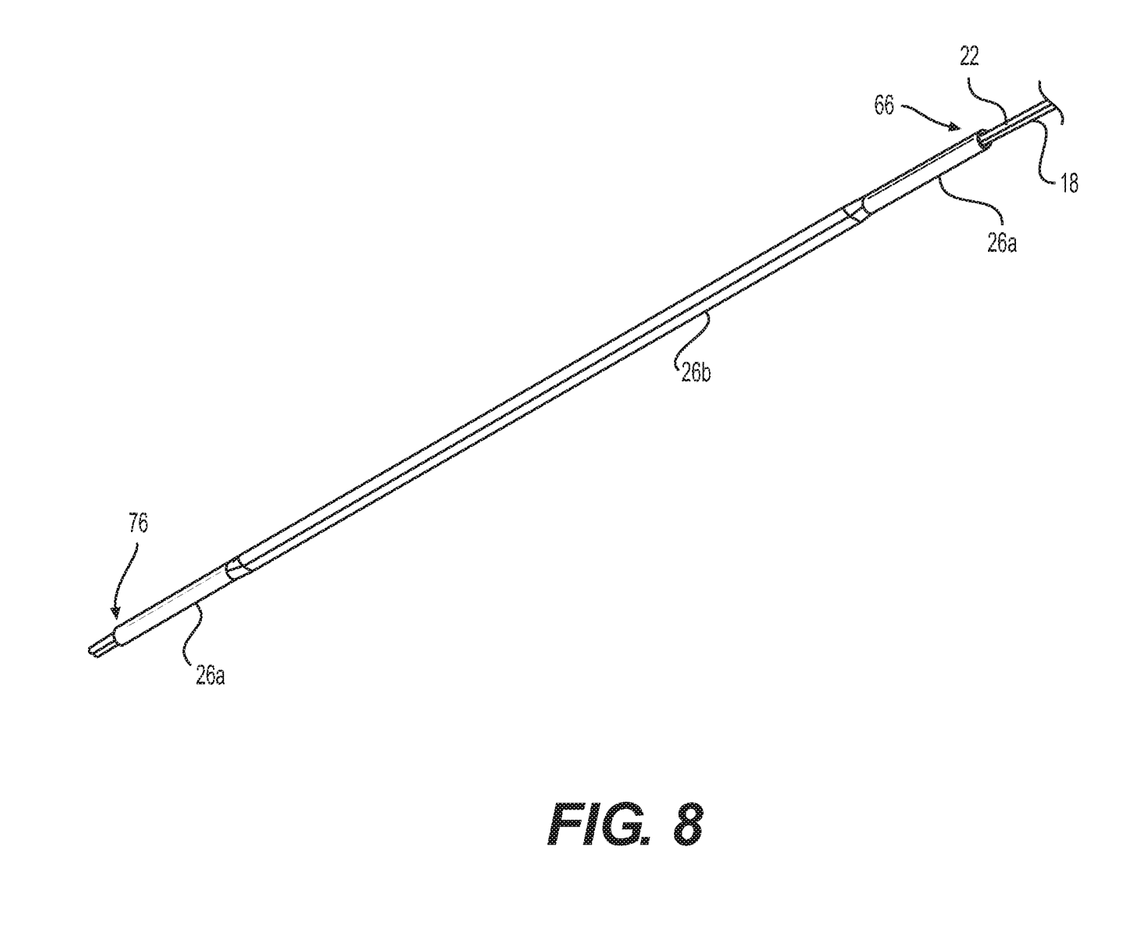
FIG. 8 is a perspective view of a support member of a retrieval device, in accordance with another example of the present disclosure.

Further, the second portions 26b, 28b, and 30b of the support members 26, 28, and 30 may each be positioned along a proximal portion, adjacent proximal ends 66, 68, and 70, respectively, of the support members while first portions 26a, 28a, and 30a of the support members 26, 28, and 30 are positioned along a distal portion, adjacent distal ends 76, 78, and 80, respectively, of the support member 26, 28, and 30, as shown in FIGS. 2, 3, 5, and 7. However, the disclosure is not so limited. Rather, second portions 26b, 28b, and 30b of the support members 26, 28, and 30 may be positioned at any location along the length of support member 26, 28, and 30. For example, as shown in FIG. 8, a central portion of each of the support member 26, 28, and 30, may be flattened such that the second portions 26b, 28b, and 30b of the support members 26, 28, and 30 may be positioned between distal and proximal first portions 26a, 28a, and 30a of the support members as shown in FIG. 8. Alternatively, the entire length of the support members 26, 28, and 30, from a proximal-most end to a distal-most end of the support members 26, 28, and 30 may be flattened (not shown). Alternatively, in some examples, multiple portions of one or more of the support members 26, 28, and 30, may be flattened such that each support member includes two or more second portions. Additionally, it is noted that the placement and/or number of second portions of at least one of the support members 26, 28, and 30 may be different than the placement and/or number of second portions of at least one other of the support members 26, 28, and 30

The support members 26, 28, and 30 may be disposed circumferentially about the longitudinal axis of the outer sheath 12, as shown in FIGS. 1-5. The longitudinal axes of the support members may be disposed at equal intervals circumferentially about the longitudinal axis. It should be noted, however, that any other suitable number of support members and spacing configurations may alternatively be utilized. As shown in FIGS. 3-6, each of the movable members 18, 20, and 22 may extend distally from a first, proximal end thereof that is coupled to the drive member 16, extend distally through a support member 26, 28, and 30, along the first leg 18a, 20a, and 22a, form the preformed U-shaped bend 18b, 20b, and 22b, and extend proximally through a different support member 26, 28, and 30 along the second leg 18c, 20c, and 22c. In this configuration, the preformed U-shaped bend may confine or urge the support members 26, 28, and 30 toward a low profile in the contracted state.

The movable members 18, 20, and 22, and the support members 26, 28, and 30, may be heat treated simultaneously, and the material for the movable members 18, 20, and 22 and the support members 26, 28, and 30 may be selected such that the support members 26, 28, and 30 will not melt during heat treatment of the movable members 18, 20, and 22. While three support members 26, 28, and 30 are shown, for example, in FIGS. 1, 2, and 4, one or more additional support members may be used.

As shown in FIG. 6, proximal portions of the support members 26, 28, and 30 may extend through the lumen 14, and may be covered by the outer sheath 12. For example, a length of about 10 millimeters of one or more of the support members 26, 28, and 30 may be covered by the outer sheath 12, leaving a length of about 9.5 millimeters exposed distal to the outer sheath 12. Distal portions of the support members 26, 28, and 30 may extend distally out of the lumen 14 and away from the distal end of the outer sheath 12. The distal portions may be configured to move towards and away from the longitudinal axis of the outer sheath 12. The number of support members 26, 28, and 30 may be equal to the number of movable members 18, 20, and 22. Alternatively, the number of support members 26, 28, and 30 may be less than the movable members 18, 20, and 22.

Each of the three support members 26, 28, and 30 may be coupled to the outer sheath 12 via an adhesive 13, such as an ultraviolet light curable adhesive or cyanoacrylate. Additionally or alternatively, the distal end of the outer sheath 12 may be fixedly coupled to the proximal ends of the support members 26, 28, and 30 by heat shrinking or by using a coupling tube glued at both ends. The coupling may keep the proximal ends of the support members 26, 28, and 30 stationary relative to the distal end of outer sheath 12, while allowing the distal ends of the support members 26, 28, and 30 to move relative to the distal end of the outer sheath 12 and relative to one another.

The first leg 18a may extend distally from the drive member 16, and may enter a lumen at the proximal end of the support member 26. The first leg 18a may extend distally through the lumen of the support member 26, and may exit the distal end of the support member 26. There, the first leg 18a may transition into the bend 18b. The bend 18b may transition into the second leg 18c. The second leg 18c may enter a lumen at the distal end of the second support member 28. The second leg 18c may extend proximally through a lumen of the second support member 28, and may exit the proximal end of the support member 28.

The first leg 20a may extend distally from the drive member 16, and may enter the lumen at the proximal end of the second support member 28. The first leg 20a may extend distally through the support member 28, and may exit the distal end of the support member 28. There, the first leg 20a may transition into the bend 20b. The bend 20b may transition into the second leg 20c. The second leg 20c may enter a lumen at the distal end of the third support member 30. The second leg 20c may extend proximally through the third support member 30, and may exit the proximal end of the third support member 30.

The first leg 22a may extend distally from the drive member 16, and may enter the lumen at the proximal end of the third support member 30. The first leg 22a may extend distally through the third support member 30, and may exit the distal end of the third support member 30. There, the first leg 22a may transition into the bend 22b. The bend 22b may transition into the second leg 22c. The second leg 22c may enter the lumen at the distal end of the first support member 26. The second leg 22c may extend proximally through the first support member 26, and may exit the proximal end of the first support member 26.

One or more of the proximal or second ends of the second legs 18c, 20c, and 22c may include a movable stop sized to abut or engage a proximal end of a support member 26, 28, and 30 after moving a distance 47 distally during movement of the retrieval device toward the expanded state. The movable stop may be formed in a number of different ways. An exemplary movable stop is shown in FIGS. 4 and 6, and includes a coupler 46 in the form of a tube including a lumen 48 configured to receive proximal ends of the second legs 18c, 20c, and 22c. The second legs 18c, 20c, and 22c may be attached to each other within the coupler 46 and attached to the coupler 46. For example, each of the second legs 18c, 20c, and 22c may be attached to each other and the coupler 46 by adhesive, melting, welding, crimping, friction fit, heat-shrinking the coupler 46, and/or any other suitable form of attachment. Portions of the first legs 18a, 20a, and 22a may extend along the side of the coupler 46, and may contact the exterior surface of the coupler 46. The coupler 46 may space portions of the first legs 18a, 20a, and 22a apart from the longitudinal axis of the outer sheath 12, to help guide the first legs 18a, 20a, and 22a into the support members 26, 28, and 30 (via first tubes 26a, 28a, and 30a, respectively).

Alternatively, the movable stop could be formed by replacing the two movable members 18 and 20 with a single moveable member having a U-shaped bend replacing the proximal ends of the second legs 18c and 20c. In this arrangement, the U-shaped bend could form the movable stop of the movable members against the proximal end of the support members 26, 28, and 30 during a first phase of the expansion of the retrieval device 10. Further, the second leg 22c could be coupled to the U-shaped bend to limit its travel. Alternatively, proximal U-shaped or L-shaped hooks, or any other type of obstruction (not shown) could be provided on one, two, or all of the second legs 18c, 20c, and 22c to form the movable stop for abutting or engaging the support members 26, 28, and 30 and limiting movement of the second legs 18c, 20c, and 22c to the distance 47 during the first phase of expansion of the retrieval device 10.

The movable members 18, 20, and 22, and the support members 26, 28, and 30, may form an end effector 50. The end effector 50 may together form the basket or grasper portion 52. In FIGS. 3-6, the grasper portion 52 is shown in the retracted and contracted state. The grasper portion 52 may be moved into its retracted and contracted state by moving the drive member 16 proximally relative to the outer sheath 12, or moving the outer sheath 12 distally relative to the drive member 16. Reference to support members 26, 28, 30 being moveable, refers to the relative movement of members 26, 28, 30 in relation to other elements of the retrieval device 10, and thus it is understood that the term "movable" includes the support members being axially stationary during movement between the contracted and expanded states, but movable radially in relation to outer sheath 12 during movement between the contracted and expanded states. In the retracted/contracted state, the bends 18b, 20b, and 22b may be at or adjacent to the distal ends of the support members 26, 28, and 30. The longitudinal axes of the support members 26, 28, and 30 may be substantially parallel, and distal portions of each of the support members 26, 28, and 30 may be in contact with the other support members. Portions of the first legs 18a, 20a, and 22a and the second legs 18c, 20c, and 22c in the lumens of respective support members 26, 28, and 30 may be substantially parallel to one another. The support members 26, 28, and 30, and/or the outer sheath 12 may help to resist bowing of the movable members 18, 20, and 22 during movement of the device between the expanded and contracted states.

In the retracted/contracted state, the distal end of the coupler 46 may be spaced from the proximal ends of the support members 26, 28, and 30 by a distance 47. The distance 47 may be about 1 millimeter, although other distances may also be used. The proximal end of the coupler 46 may be spaced from the distal end of the sleeve 24 by a distance 49. The distance 49 may be about 16 millimeters, although other distances may also be used. In another example, distance 49 may be about 11 millimeters. Other distances 49 may position sleeve 24 in a more proximal position relative to a flexible ureteroscope channel where the ureteroscope scope does not deflect. This positioning may prevent binding of sleeve 24 within a curved portion of sheath 12. However, it is also contemplated that sleeve 24 may include one or more flexible materials. The distances 47 and 49 may vary based on the procedure being performed with the retrieval device 10.

In FIGS. 1 and 2, the retrieval device 10 is shown with the grasper portion 52 in an extended and expanded state. In the extended and expanded state, portions of the movable members 18, 20, and 22 may be exposed from the distal ends of the support members 26, 28, and 30 and the outer sheath 12. Once exposed, one or more of the movable members 18, 20, and 22 may move radially outwardly from the longitudinal axis of the outer sheath 12 due to a natural and/or applied radially outward biasing in one or more of the movable members 18, 20, and 22. Radially outward movement of one or more of the movable members 18, 20, and 22 may cause a corresponding radially outward movement of the support members 26, 28, and 30.

Referring to FIG. 2, the exposed portions of the movable members 18, 20, and 22 may form bridges 62, 64, and 66 between the distal ends of the support members 26, 28, and 30. Each bridge may extend distally from the distal end of a given support member 26, 28, 30, and may be received in the distal end of an adjacent support member 26, 28, 30. The bridges 62, 64, and 66 may be formed by distal portions of the first legs 18a, 20a, and 22a, the bends 18b, 20b, and 22b, and distal portions of the second legs 18c, 20c and 22c.

Each bridge and its corresponding two support members may form a side loop of the grasper portion 52. Three side loops 54, 56, and 58 are shown in FIG. 2. The bridges 62, 64, and 66 may form a front loop 60 of the grasper portion 52 (a front loop 60 facing distally). Materials may enter the grasper portion 52 through one or more of the front loop 60 and the side loops 54, 56, and 58. By adding additional movable members and support members, additional side loops can be created.

Relative movement between drive member 16 and outer sheath 12 may cause grasper portion 52 to move to its extended and expanded state due to a natural and/or applied radially outward biasing in one or more of the movable members 18, 20, and 22. Extension and expansion of the grasper portion 52 may occur in phases. Starting from the retracted and contracted state shown in FIG. 3, a first phase of the extension and expansion of the grasper portion 52 may begin with movement of the drive member 16 distally relative to the outer sheath 12 and the support members 26, 28, and 30. The relative movement of the drive member 16 may cause the movable members 18, 20, and 22 and the coupler 46 to move distally relative to the outer sheath 12. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move distally relative to the outer sheath 12 and support members 26, 28, and 30 during the first phase. Proximal portions of the first legs 18a, 20a, and 22a and second legs 18c, 20c, and 22c may enter the lumens at the proximal end of support members 26, 28, and 30. Distal portions of the first legs 18a, 20a, and 22a, bends 18b, 20b, and 22b, and second legs 18c, 20c, and 22c may emerge from, or extend further out from, the distal ends of the support members 26, 28, and 30.

The coupler 46 forming the movable stop moves with the movable members 18, 20, and 22 relative to the outer sheath 12 and support members 26, 28, and 30. When the coupler 46 has traveled the distance 47 relative to the outer sheath 12 and support members 26, 28, and 30, further distal movement of the coupler 46 may be halted as the coupler 46 approaches the proximal ends of the support members 26, 28, and 30. This prevents the second legs 18c, 20c, and 22c from further entering the lumens of second tubes 28b, 30b, and 26b. At the end of the first phase of extension and expansion, the bends 18b, 20b, and 22b may each be spaced from distal ends of the support members 26, 28, and 30 by the distance 47 because the U-shaped bends 18b, 20b, and 22b are located a fixed distance from the coupler 46.

The presence of distance 47 between the support members 26, 28, and 30, and the coupler 46 facilitates the reciprocal movement of retrieval device 10 between the contracted and expanded states. That is, the presence of distance 47 reduces an initial amount of force required to move retrieval device 10 from the contracted state toward the expanded state. As described above, movable members 18, 20, and 22 may include a preset U-shape bend 18b, 20b, and 22b that serves to help clamp the distal end of the support members 26, 28, and 30 in the contracted state. By extending the movable members 18, 20, and 22 the distance 47, the clamping resistance of the U-shaped bends 18b, 20b, and 22b on the distal ends of the support members 26, 28, and 30 may be reduced. Moreover, movement of the movable members 18, 20, and 22 away from the distal end of the support members 26, 28, and 30 may provide a greater moment arm to overcome the bias of the U-shaped bends 18b, 20b, and 22b when moving the retrieval device 10 toward the expanded state.

The presence of distance 47 may also permit retrieval device 10 to form a first stage grasper by the portion of the movable members 18, 20, and 22 extending distally of the support members 26, 28, and 30. This first stage grasper can capture smaller fragments within only the portion of movable members 18, 20, and 22 extending distally from support members 26, 28, and 30 after movement of the distance 47. The distal ends of movable members 18, 20, and 22 may more securely capture smaller fragments than support members 26, 28, and 30 because they include a more distributed contact array or wire web than the support members 26, 28, and 30. It is noted that during the first phase movement of the movable members 18, 20, and 22, the support members extend generally parallel to one another. As understood, the word "generally" as used herein means mainly, and if more specificity is required, means a range of plus or minus eight percent of the relevant value.

A second phase of the extension and expansion of the grasper portion 52 may begin after distal movement of the coupler 46 has been halted. During the second phase, further distal movement of the drive member 16 relative to the outer sheath 12 and support members 26, 28, and 30 may drive distal movement of the first legs 18a, 20a, and 22a relative to the outer sheath 12 and support members 26, 28, and 30. During the second phase, the second legs 18c, 20c, and 22c may remain stationary relative to the support members 26, 28, and 30. The first legs 18a, 20a, and 22a may be increasingly exposed from the distal ends of the support members 26, 28, and 30, thereby increasing the lengths of the bridges 62, 64, and 66. Distal portions of the movable members 18, 20, and 22, and the support members 26, 28, and 30, may expand radially outwardly. The front loop 60 and the side loops 54, 56, and 58 may also expand in size.

Extension and expansion in the second phase may continue over the distance 49. Once the first legs 18a, 20a, and 22a have traveled the distance 49, distal movement of the drive member 16 may halt. Distal movement of the drive member 16 may be halted, for example, by a stop formed in the handle assembly shown in FIG. 1.

Moving the grasper portion 52 back to the retracted and contracted state may be accomplished by moving the drive member 16 proximally relative to the outer sheath 12 and support members 26, 28, and 30. Movement from the extended and expanded state to the retracted and contracted state may also occur in phases. A first phase of the retraction and contraction of the grasper portion 52 may begin with the drive member 16 moving proximally relative to the outer sheath 12. This may cause the first legs 18a, 20a, and 22a to move proximally relative to the outer sheath 12 and support members 26, 28, and 30. Distal portions of the first legs 18a, 20a, and 22a may enter the lumens at the distal ends of the support members 26, 28, and 30. The second legs 18c, 20c, and 22c, and the coupler 46 may remain stationary relative to the support members 26, 28, and 30. The lengths of the bridges 62, 64, and 66 may decrease. The first legs 18a, 20a, and 22a, second legs 18c, 20c, and 22c, and support members 26, 28, and 30 may move radially inwardly. Thus, the front loop 60 and the side loops 54, 56, and 58 may decrease in size.

The first phase of the retraction and contraction of the grasper portion 52 may take place over the distance 49. Once the distance 49 has been covered, a second phase of the retraction and contraction may take place with continued movement of the drive member 16 proximally relative to the outer sheath 12 and the support members 26, 28, and 30. The continued movement may cause the movable members 18, 20, and 22 and the coupler 46 to move distally relative to the outer sheath 12 and support members 26, 28, and 30. The movement of the drive member 16, movable members 18, 20, and 22, and coupler 46 may be translational. For example, the drive member 16, first legs 18a, 20a, and 22a, bends 18b, 20b, and 22b, second legs 18c, 20c, and 22c, and coupler 46, may move proximally relative to the outer sheath 12 and the support members 26, 28, and 30 during the second phase. Distal portions of the first legs 18a, 20a, and 22a may enter into, or move further past the distal ends of the support members 26, 28, and 30, while the second legs 18c, 20c, and 22c may enter into, or move further past, the distal ends of the support members 26, 28, and 30. The lengths of the bridges 62, 64, and 66 may decrease as the exposed lengths of the movable members 18, 20, and 22 decrease. As the bridges 62, 64, and 66 shrink, distal portions of the movable members 18, 20, and 22, and the support members 26, 28, and 30, may contract radially inwardly toward the longitudinal axis of the outer sheath 22. The front loop 60 and side loops 54, 56, and 58 may also shrink in size.

The coupler 46 may move with the movable members 18, 20, and 22 relative to the outer sheath 12 and support members 26, 28, and 30. When the coupler 46 has traveled the distance 47 relative to the outer sheath 12 and support members 26, 28, and 30, further proximal movement of the coupler 46 may be halted by operation of the handle assembly 90, such as a stop formed in the handle assembly 90 of FIG. 1. At the end of the second phase of retraction and contraction, the state shown in FIGS. 3-6 is attained. As noted above, in this contracted state, movable members 18, 20, and 22 may include preset U-shape bends 18b, 20b, and 22b located adjacent the distal ends of the support members 26, 28, and 30 that serve to help clamp the distal end of the support members 26, 28, and 30 in the contracted state.

Referring back to FIG. 1, the handle assembly 90 may be disposed at the proximal end 86 of the retrieval device 10. Handle assembly 90 may include the actuator 92 such as, e.g., a sliding mechanism, rotating mechanism, pushing mechanism, or the like. Actuator 92 may be coupled to outer sheath 12 and include internal stops for limiting movement of the outer sheath 12 relative to the movable members 18, 20, and 22. The drive member 16 may be fixed to a proximal end of the handle assembly 90. It is understood that the handle assembly may be formed in any conventional manner to control the movement of movable members 18, 20, and 22 relative to the outer sheath 12 and support members 26, 28, and 30 as described above. As noted above, handle assembly 90 may include one or more internal or external stops to limit movement of the movable members 18, 20, and 22.

The disclosed retrieval devices may be utilized in any suitable application requiring the capture and removal of materials from the body. Any aspect set forth in any example may be used with any other example set forth herein. The devices may be used in any suitable medical procedure, may be advanced through any suitable body lumen and body cavity, and may be used to remove material from any suitable body portion. For example, the devices described herein may be used through any natural body lumen or tract, including those accessed orally, vaginally, rectally, nasally, urethrally, or through incisions in any suitable tissue.

The disclosed devices may be configured to capture fragments having dimensions of about 3 French or smaller. In some examples, the disclosed medical devices may be able to capture and release smaller stones having diameters from 1 millimeter to 12 millimeters. In some examples, a user may want to reposition larger stones from the lower calyx to the upper calyx of the kidney to be broken with a laser before removing them through a small diameter of the ureter. The stones may be removed in front of a scope, as opposed to through scope channel to prevent damage to a scope channel. When stones are removed, both an endoscope and the retrieval device may be removed from the human body. In some examples, a guide sheath for a ureteroscope may be used to guide the ureteroscope and retrieval device back to a previous position or to a new position to capture additional stones, and protect a ureter wall during stone removal. While moving from the extended and expanded state to the retracted and contracted state, retrieval devices of the present disclosure may ligate larger stones and capture smaller stones within the grasper portion 52.

It will be apparent to those skilled in the art that various modifications and variations can be made in the disclosed systems and processes without departing from the scope of the disclosure. For example, the retrieval device disclosed could include more than three support members, such as four or five support members, and an equal number or less movable members. Other examples of the disclosure will be apparent to those skilled in the art from consideration of the specification and practice of the features disclosed herein. It is intended that the specification and examples be considered as exemplary only.

I claim:

1. A retrieval device having a contracted state and an expanded state, comprising:
   a sheath;
   at least three support members each having a first portion with a first cross-sectional shape being distal to a second portion with a second cross-sectional shape different from the first cross-sectional shape, a proximal end fixed to the sheath, and a distal end movable relative to the sheath; and
   at least three movable members each having a pair of ends movable relative to the support members, each movable member extending through a lumen of one support member of the at least three support members and through a lumen of a different support member of the at least three support members, wherein the first portion is sized to permit a plurality of degrees of freedom to each movable member; and
   wherein the second portion is sized to permit a reduced number of degrees of freedom to each movable member so as to prevent a first movable member from twisting about another moveable member of the at least three moveable members.

2. The retrieval device of claim 1, wherein the first cross-sectional shape is circular and the second cross-sectional shape is ovular.

3. The retrieval device of claim 1, wherein the first portion is positioned adjacent the distal end and the second portion is positioned adjacent the proximal end.

4. The retrieval device of claim 1, wherein the second portion is positioned along the support member between two separate and distinct first portions.

5. The retrieval device of claim 1, wherein each support member is comprised of polyimide, PET, or combinations thereof.

6. The retrieval device of claim 1, further including a transition portion between the first portion and the second portion of each of the support members.

7. The retrieval device of claim 1, wherein each of the at least three movable members are configured to slide distally within one or more of the at least three support members during transition of the retrieval device from the contracted state to the expanded state.

8. The retrieval device of claim 1, wherein each support member is parallel to a longitudinal axis of the sheath while the retrieval device is in the contracted state.

9. The retrieval device of claim 1, wherein each support member is configured to bow radially outward from a longitudinal axis of the sheath in the expanded state.

10. The retrieval device of claim 1, wherein the sheath encompasses at least a portion of the movable members and at least a portion of the support members.

11. The retrieval device of claim 1, further including a stop located at an end of at least one movable member to restrict movement of the end after moving a distance distally.

12. The retrieval device of claim 11, wherein the stop includes a coupling securing at least one end of the pair of ends of each of the at least three movable members together.

13. The retrieval device of claim 1, wherein each of the at least three movable members includes a U-shaped bend located distally of the distal ends of the at least three support members.

14. The retrieval device of claim 13, wherein the U-shaped bend is preformed and urges the support members toward the contracted state.

15. A retrieval device, comprising:
   a sheath;
   at least three support members each tapering from a first portion with a circular cross-sectional shape to a second portion with a ovular cross-sectional shape, wherein each of the support members is movable between a contracted configuration extending along a longitudinal axis of the sheath in the contracted configuration, and an expanded configuration bowing radially outward from the longitudinal axis of the sheath; and
   at least three movable members, each movable member forming a bridge between two different support members of the at least three support members, wherein each of the at least three movable members includes a first end and a second end, and wherein each of the first end and the second end are moveable relative to the at least three support members.

16. The retrieval device of claim 15, wherein the first portion is positioned adjacent a distal end of the support members and the second portion is positioned adjacent a proximal end of the support members.

17. The retrieval device of claim 15, wherein the retrieval device includes three bridges formed by the at least three movable members, wherein the three bridges form a distally-facing loop when the support members are in the expanded configuration.

18. The retrieval device of claim 15, wherein each bridge forms a side loop with the two different support members that the bridge is between.

19. A method for retrieving an object using a retrieval device including a sheath, at least three support members each having a varied cross-sectional shape along a length of the support members, a proximal end fixed to the sheath, and a distal end movable relative to the sheath, and at least three movable members movable relative to the support members, each movable member extending through a lumen of one support member of the at least three support members and through a lumen of a different support member of the at least three support members, the method comprising:

moving first and second ends of the movable members distally to transition the retrieval device from a contracted state to an expanded state.

20. The method of claim 19, wherein a first portion of at least one of the support members is sized to permit a plurality of degrees of freedom to each movable member located within the first portion, a second portion of the at least one of the support members is sized to permit a reduced number of degrees of freedom to each movable member so as to prevent a first movable member from twisting about another movable member of the at least three movable members.

* * * * *